United States Patent
Suh et al.

(10) Patent No.: US 10,226,284 B2
(45) Date of Patent: Mar. 12, 2019

(54) LAMINOPLASTY PLATES, SYSTEMS, AND DEVICES, AND METHODS RELATING TO THE SAME

(75) Inventors: Jon Suh, Blue Bell, PA (US); Sean Suh, Bensalem, PA (US)

(73) Assignee: Globus Medical, Inc., Audubon, PA (US)

( * ) Notice: Subject to any disclaimer, the term of this patent is extended or adjusted under 35 U.S.C. 154(b) by 34 days.

(21) Appl. No.: 13/224,093

(22) Filed: Sep. 1, 2011

(65) Prior Publication Data

US 2013/0060283 A1 Mar. 7, 2013

(51) Int. Cl.
*A61B 17/70* (2006.01)
*A61B 17/80* (2006.01)

(52) U.S. Cl.
CPC ...... *A61B 17/7071* (2013.01); *A61B 17/7007* (2013.01); *A61B 17/809* (2013.01)

(58) Field of Classification Search
CPC . A61B 17/70; A61B 17/7007; A61B 17/7071; A61B 17/809
USPC ............ 606/70–71, 280–299, 903–906; 623/17.11, 17.13, 17.15–17.16
See application file for complete search history.

(56) References Cited

U.S. PATENT DOCUMENTS

| | | | |
|---|---|---|---|
| 6,066,175 A | 5/2000 | Henderson | |
| 6,080,157 A | 6/2000 | Cathro | |
| 6,235,059 B1 | 5/2001 | Benezech | |
| 6,572,619 B2 | 6/2003 | Santilli | |
| 6,576,017 B2 * | 6/2003 | Foley et al. | 623/17.16 |
| 6,635,087 B2 * | 10/2003 | Angelucci et al. | 623/17.11 |
| 6,660,007 B2 | 12/2003 | Khanna | |
| 7,112,222 B2 * | 9/2006 | Fraser et al. | 623/17.11 |
| 7,182,782 B2 * | 2/2007 | Kirschman | 623/17.11 |
| 7,264,620 B2 * | 9/2007 | Taylor | 606/86 A |
| 8,641,766 B2 * | 2/2014 | Donner | A61B 17/70 606/246 |
| 8,926,664 B1 * | 1/2015 | Millhouse | A61B 17/7071 606/246 |
| 2002/0120335 A1 | 8/2002 | Angelucci | |
| 2004/0030388 A1 * | 2/2004 | Null | A61B 17/7059 623/17.11 |
| 2005/0250379 A1 * | 11/2005 | Coffey | H01R 13/741 439/544 |
| 2005/0251138 A1 * | 11/2005 | Boris et al. | 606/61 |
| 2009/0210009 A1 * | 8/2009 | Chao et al. | 606/280 |
| 2009/0210012 A1 * | 8/2009 | Null et al. | 606/280 |
| 2010/0161056 A1 * | 6/2010 | Voellmicke et al. | 623/17.11 |

(Continued)

*Primary Examiner* — Eric S Gibson
*Assistant Examiner* — Marcela I Shirsat (57) ABSTRACT

Disclosed are laminoplasty devices and systems, kits that include such laminoplasty devices or systems or components thereof; and methods of assembling and using such laminoplasty devices and systems. In particular, articulating laminoplasty devices are provided that allow lamina plates to be adjusted angularly and transitionally with respect to a cage connecting the lamina plates. Also provided are laminoplasty plates that are configured so as to be assembled with a bone graft housing, and which provide an opening configured to facilitate bone graft insertion into the housing. Further provided are expandable laminoplasty fixation systems that include a lateral mass plate, a lamina plate and a set screw that when screwed and unscrewed, allows one to contract and expand the plates with respect to one another.

18 Claims, 12 Drawing Sheets

(56) References Cited

U.S. PATENT DOCUMENTS

| | | |
|---|---|---|
| 2011/0106083 A1 | 5/2011 | Voellmicke |
| 2011/0106087 A1* | 5/2011 | Gamache |
| 2011/0106169 A1* | 5/2011 | Zalenski et al. ............. 606/279 |
| 2011/0178599 A1* | 7/2011 | Brett ...................... A61F 2/442 623/17.16 |
| 2012/0165942 A1* | 6/2012 | Khanna ............. A61B 17/7071 623/17.16 |

* cited by examiner

LAMINOPLASTY PLATES, SYSTEMS, AND DEVICES, AND METHODS RELATING TO THE SAME

FIELD OF THE INVENTION

The present invention generally relates to devices and methods for treating degenerative conditions of the spine and/or for alleviating pain or discomfort associated with the spinal column. More specifically, the present invention is directed to laminoplasty plates, systems, and devices, and kits and methods relating to the same.

BACKGROUND

In certain circumstances, the spinal canal extending through a patient's vertebrae is or becomes too narrow and constricts the spinal cord extending therethrough. Narrowing can be attributable to causes such as age, injury or removal of a spinal disk.

For instance, cervical spondylosis is a common degenerative condition of the cervical spine that most likely is caused by age-related changes in the intervertebral disks. As disk degeneration occurs, mechanical stresses result in osteophytic spurs, which may form along the interior aspect of the spinal canal and can compress the spinal cord. The constriction of the spinal cord in the cervical spine, for example, often produces pain, weakness, or loss of feeling in extremities. Other causes for narrowing of the spinal canal include disc shrinkage, which causes the disc space to narrow and the annulus to bulge and mushroom out, resulting in pressure on the spinal cord. Degenerative arthritis of facet joints can cause joints to enlarge, or the vertebra to slip with respect to each other, also compressing the spinal cord. Instability between vertebrae, such as caused by stretched and thickened ligaments can also produce pressure on the spinal cord and nerve roots.

Myelopathy, or affliction or injury of the spinal cord, occurs due to its compression. The rubbing of the spine against the cord can also contribute to this condition, and the spinal cord compression can ultimately compromise the blood vessels feeding the spinal cord, further aggravating the myelopathy.

Traditional procedures for decompressing the spinal cord include a laminectomy and a laminoplasty. In a laminectomy, the lamina and spinal processes are removed to expose the dura covering the spinal cord. Another known procedure is a laminoplasty, in which the lamina is lifted off the dura, but is not completely removed. According to one laminoplasty procedure sometimes referred to as an "open door" procedure, an osteotomy is performed in which a complete cut is made through one side of the vertebra, approximately between the lamina and lateral mass, while a partial-depth cut is made on the opposite lateral side. The lamina is then hinged open about the partial cut to increase the cross-sectional size of the spinal canal to decompress the spinal cord therein. In certain procedures, a laminoplasty plate is then fixed between the facet and the hinged open lamina. According to some known methods, the plate of an appropriate size is selected and bent to the desired shape and generally has a plurality of screw holes. In other techniques, a strut of bone may be placed in the open portion within the lamina and the facet to help hold the open position of the lamina. In general, prior to the operation, the surgeon needs to measure the vertebra to determine the size of the plate necessary for implantation. At that point, a plate can be selected with the appropriate dimensions, and implanted at the site.

SUMMARY OF THE INVENTION

Improved laminoplasty plates and devices are needed. For example, a laminoplasty device that may be articulated, expandable, and/or malleable may be desired to achieve a better fit with respect to varying individual anatomical landmarks, so that a plate does not have to be custom selected and intensively shaped and formed prior to each surgery.

Example embodiments herein are generally related to laminoplasty plates, devices, systems, methods of making and using the same. The plates, devices, systems, and methods herein may be used to reduce or eliminate excess compression, constriction and/or other pressure on the spinal cord and/or nerve roods, caused e.g., by spurs, disc shrinkage, enlarged joints, thickened ligaments etc.

Non-limiting example embodiments include for example, articulating laminoplasty devices, which include a cage connecting one or more lamina plates. The one or more lamina plates may be attached to the cage by a slotted hinge, which allows the lamina plates to be adjusted angularly and/or transitionally with respect to the cage. At least one of the lamina plates may include one or more openings adapted for receiving a bone fastener, such as a bone screw.

Other non-limiting example embodiments include a laminoplasty plate that includes at least one opening configured in size, position and shape, to facilitate bone graft insertion into a bone graft housing when the laminoplasty plate is attached to the bone graft housing. Such plates may include one or more screw holes adapted for receiving a bone fastener disposed on each end of the laminoplasty plate. Also included are systems that include the plate and at least one bone graft housing, which are each configured to be attached to one another.

Further non-limiting example embodiments include an expandable laminoplasty fixation system comprising a lateral mass plate having a set screw housing; a lamina plate having angled grooves; and a set screw positioned at least partially within said set screw housing, wherein said set screw has set screw thread, which thread is mated with the angled grooves of the lamina plate, such that when the screw is screwed or unscrewed, the screwing and unscrewing causes the lateral mass plate and lamina plate to contract or expand with respect to one another.

Other example embodiments are directed to kits or systems that include the present plates, devices, systems, or kits, or components thereof; and may further include e.g., tools for assembling and/or inserting the present devices, instructions for use, or other components that may be useful in making and/or using the plates, devices, systems, or kits.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF THE FIGURES

Non-limiting example embodiments described herein, with reference to the following accompanying Figures.

FIG. 7 depicts a side (7A) and perspective (7B and 7C) views of an expandable laminoplasty fixation device according to non-limiting embodiments of the invention, in several positions;

DETAILED DESCRIPTION

The aspects, advantages and/or other features of example embodiments of the invention will become apparent in view of the following detailed description, taken in conjunction with the accompanying drawings. In describing example embodiments, specific terminology is employed for the sake of clarity. However, the embodiments are not intended to be limited to this specific terminology. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. It is to be understood that each specific element includes all technical equivalents that operate in a similar manner to accomplish a similar purpose.

Unless otherwise noted, technical terms are used according to conventional usage. Any patents and/or publications mentioned in this specification are indicative of the level of those skilled in the art to which the invention pertains. All publications, patent applications, patents, and other references mentioned herein are incorporated by reference in their entirety.

As used herein, "a" or "an" may mean one or more. As used herein, "another" may mean at least a second or more. Furthermore, unless otherwise required by context, singular terms include pluralities and plural terms include the singular.

Generally provided herein are laminoplasty plates, systems and devices, which provide flexibility, expandability, and customizability to conform the plates, systems and devices to a patient during a laminoplasty procedure. Also provided herein are kits that include such laminoplasty plates, systems and/or devices, or components thereof. Further provided are methods of assembling the present laminoplasty plates, systems and devices, and laminoplasty methods which include using the present laminoplasty plates, systems and devices.

Figure 1A:
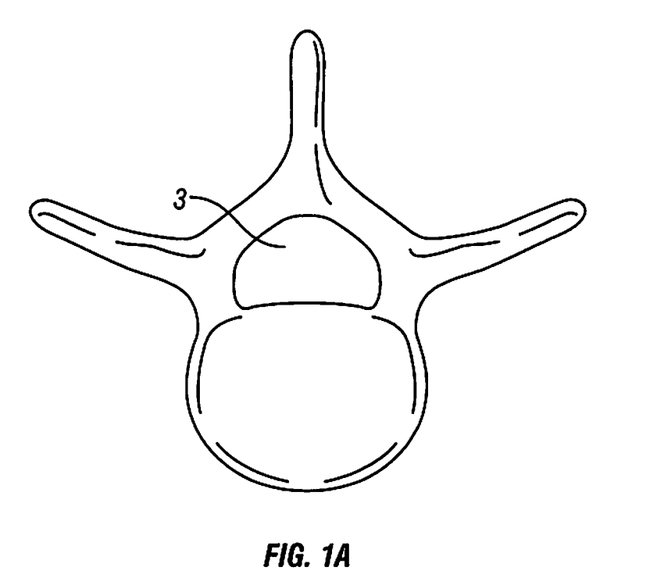
FIGS. 1A and 1B are view of a vertebral body prior to and after one complete cut and one partial cut are made in the vertebral body, and lamina is hinged as part of an "open door" laminoplasty procedure.
Figure 1B:
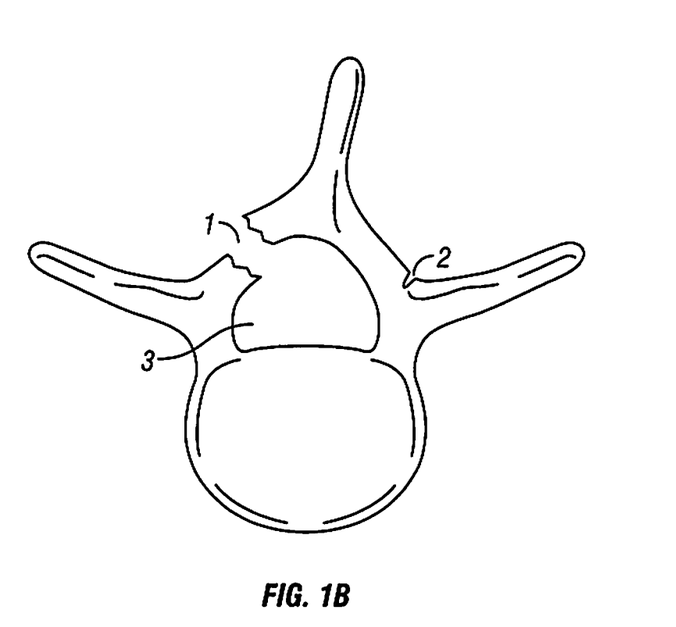

FIGS. 2-11 depict embodiments of plates, devices, systems, or implants for use in a unilateral or "open door" laminoplasty procedure are shown. Generally, in an "open door" laminoplasty procedure, an osteotomy is performed in which a complete cut 1 is made through one side of the vertebra, approximately between the lamina and lateral mass, while a partial-depth cut 2 is made on the opposite lateral side. (FIGS. 1A and 1B) The lamina is then hinged open about the partial cut to enlarge the spinal canal 3. The present laminoplasty plates, devices, systems, or implants are then attached to the lamina to maintain the lamina in a desired position.

Example embodiments herein include articulating lamina devices, which may be used to address situations e.g., in which rigid lamina plates do not conform to varying anatomical landmarks of individual patients. The embodiments depicted in FIGS. 2A-C for example, provide an articulating lamina device cage construct with pivoting and twisting capability for better fit on varying individual anatomical landmarks.

In particular, non-limiting example embodiments provided herein include articulating laminoplasty devices, which include a cage connecting one or more lamina plates. The one or more lamina plates may each be attached to the cage, e.g. on opposite sides of the cage; by a slotted hinge, which slotted hinges may allow the lamina plates to be adjusted angularly and/or transitionally with respect to the cage. At least one of the lamina plates may include one or more openings adapted for receiving a bone fastener, such as a bone screw to attach the lamina plates to a patients' lamina.

Figure 2A:
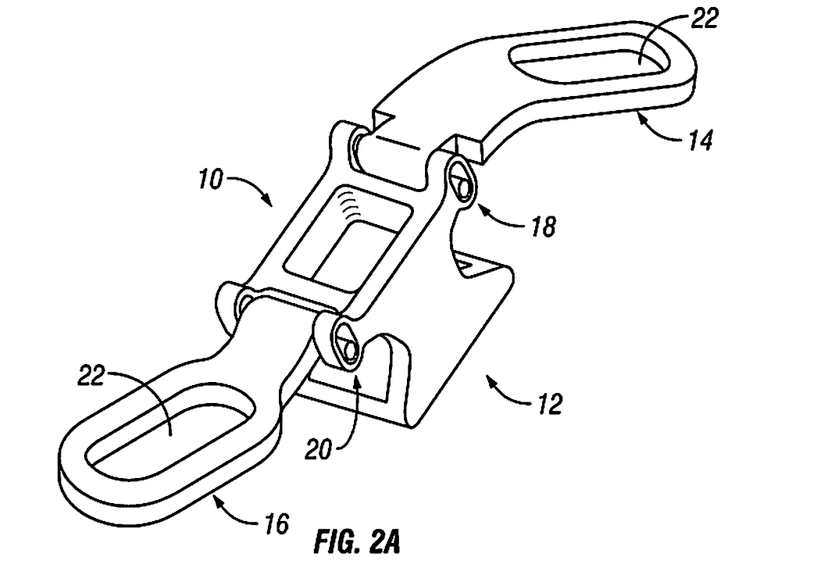
FIG. 2A is a perspective view of an articulating laminoplasty device according to non-limiting embodiments of the invention.
Figure 2B:
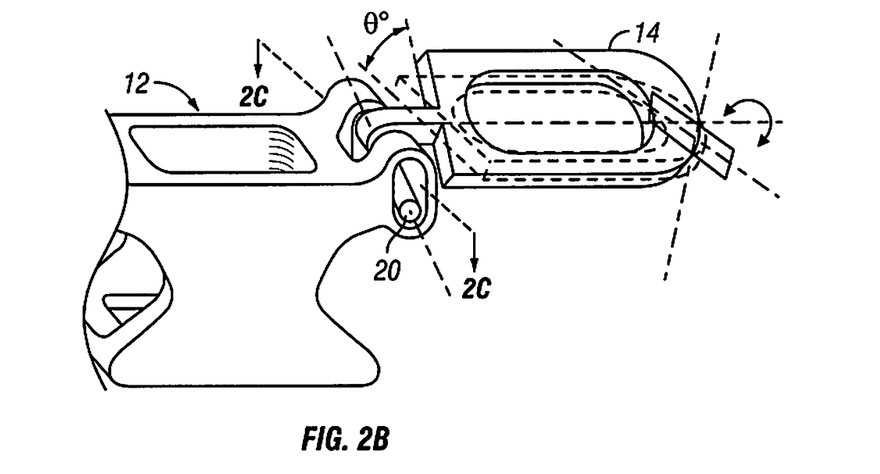
FIG. 2B is another perspective view of a portion of the articulating laminoplasty device depicted in FIG. 2A, according to non-limiting embodiments of the invention.
Figure 2C:
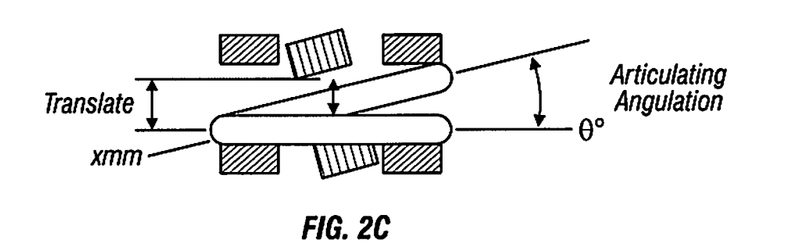
FIG. 2C depicts various forms of movement and adjustment that may be achieved by the device of FIGS. 2A and 2B.

Referring to FIGS. 2A-2C non-limiting exemplary embodiments of an articulating laminoplasty device 10 according to the invention is shown. According to these embodiments, an articulating laminoplasty device 10 includes a cage 12 connecting a first lamina plate 14 and a second lamina plate 16 to the cage 12. According to these embodiments a slotted hinge 18 is provided where each of the first and second lamina plates 14, 16 are connected to the cage 12, e.g., by hinge pins 20. As depicted in FIGS. 2B and 2C, embodiments having at least one slotted hinge may allow angular adjustment as well as transitional adjustment of one or both lamina plates, for ease of contour fitting to a patient.

Lamina plates 12 and 14 may each include one or more openings or holes 22 for receiving a bone fastener, such as a bone screw. The holes 22 may be disposed for example for accessing and inserting the fasteners from the outside of the bone to facilitate implantation. According to non-limiting embodiments, articulating lamina plate devices herein may be configured for use in an "open door" laminoplasty procedure with a first lamina plate 14 configured for securing to a portion of a lamina that has been cut and hinged away from the lateral mass.

In example embodiments, the cage 12 is a non-load bearing lamina cage. The cage may be configured for ease of anatomical fit without a secondary twisting or bending of the plate.

According to non-limiting example embodiments, at least one bone strut may be attached to an inner surface of plate 14 and/or 16 to facilitate bone fusion or regeneration between the lateral mass and lamina.

According to non-limiting example embodiments, one or more of the present lamina plates may be made from one or more materials that would be suitable for implantation into a subject, such as a human, including for example, titanium material. In alternate embodiments any other suitable implant material known to those skilled in the art may be used.

Non-limiting example embodiments may also include methods that include inserting the present articulating laminoplasty device into a patient, adjusting the lateral and or transitional position of one or more lamina plates with respect to a lamina cage, to fit a patient into which the articulating laminoplasty device is inserted, and fixing the lamina plates to the patients lamina in a desired position, e.g., using bone fasteners.

FIGS. 3-6 depict non-limiting example embodiments of laminoplasty plates of the present invention. Further example embodiments include systems that include both the laminoplasty plates and an attachable bone graft housing. Thus, encompassed herein are the laminoplasty plates themselves, as well as devices, systems, kits and methods that include one or both of a laminoplasty plate and a bone graft housing either apart or attached to one another.

Figures 3A, 3B, 3C:
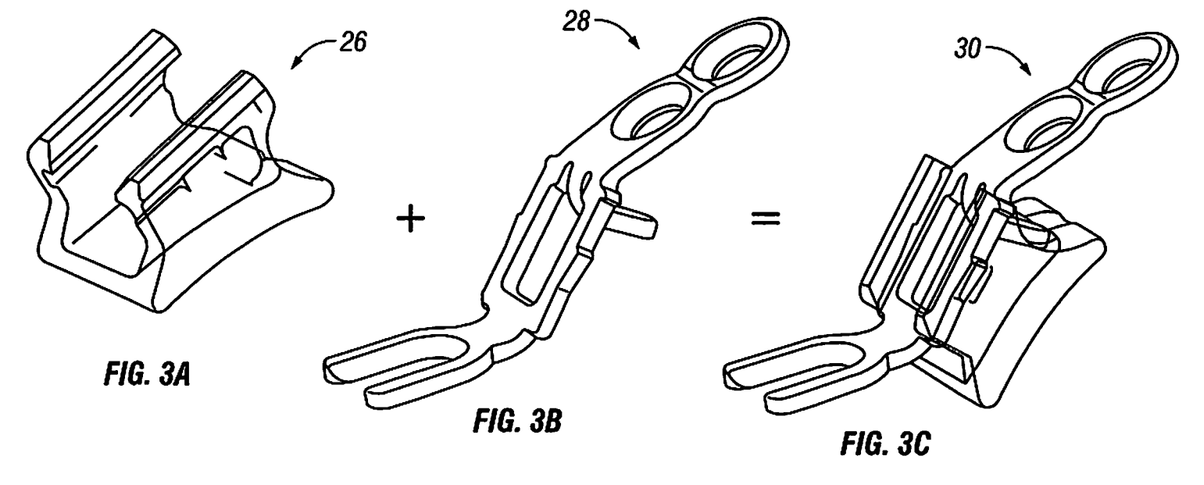
FIGS. 3A-3C depict a bone graft housing (3A) and laminoplasty plate (3B) separately and assembled together (3C) according to non-limiting embodiments of the invention.

FIG. 3 depicts an example bone graft housing 26, which may be combined with a laminoplasty plate 28 in accordance with embodiments of the present invention to form a plate and housing system or assembly 30. Laminoplasty plates in accordance with the present invention may include a least one opening 32 to facilitate bone graft insertion into the housing 26. The plate may or may not have an upper and/or lower finger to sustain the plate between lamina and lateral mass after insertion of the plate into a patient.

Non-limiting example embodiments are directed to laminoplasty plates that include at least one opening configured in size, position, and shape, to facilitate bone graft insertion into a bone graft housing when the laminoplasty plate is attached to the bone graft housing; and one or more screw holes disposed on each end of the laminoplasty plate, which screw holes are adapted for receiving a bone fastener or screw. Further example embodiments include laminoplasty systems that include a laminoplasty plate and an attachable bone graft housing.

The bone graft housing and laminoplasty plate may be configured so as to allow one to assemble the laminoplasty plate and bone graft housing in the operating room. By way of non-limiting example, the plate and housing may be assembled in an operating room by sliding a laminoplasty plate into a housing or alternatively, by snapping the plate on a housing, and locking the plate in place. Accordingly, example methods include sliding a laminoplasty plate into a bone graft housing and securing or locking the laminoplasty plate to the bone graft housing. As described with respect to further embodiments below, an example lock may include a portion of the laminoplasty plate that fits within one or more openings in the bone graft housing. As also described below, the bone graft housing may also include one or more stops to hold the laminoplasty plate in a desired position within the housing.

Also encompassed are methods that include inserting a laminoplasty plate/bone graft housing system into a patient and fixing the system to the patient's lamina in a desired position, e.g., using bone fasteners.

Figure 4:
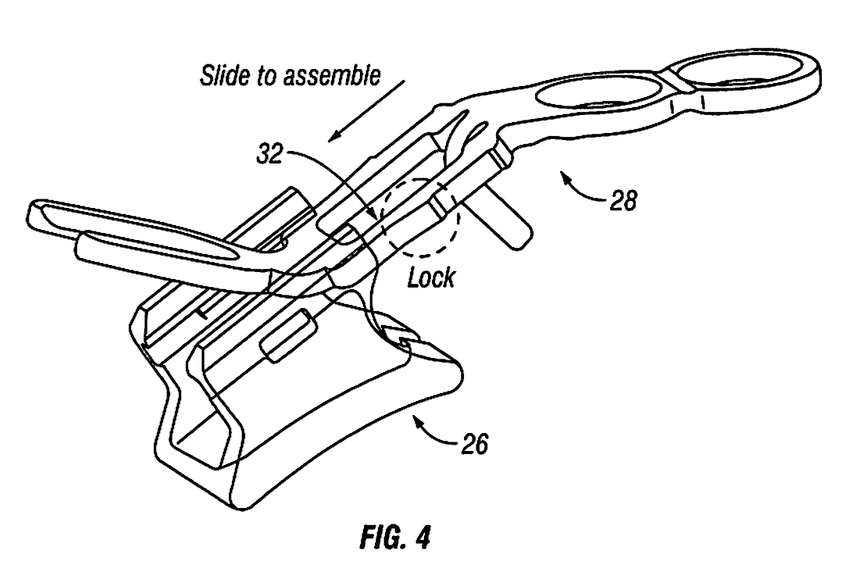
FIG. 4 depicts a perspective view during an assembly process in which a laminoplasty plate is being slid into a bone graft housing according to non-limiting embodiments of the invention.

FIG. 4 depicts an example embodiment in which a laminoplasty plate 28 is being slid into a bone graft housing 26.

Figure 5:
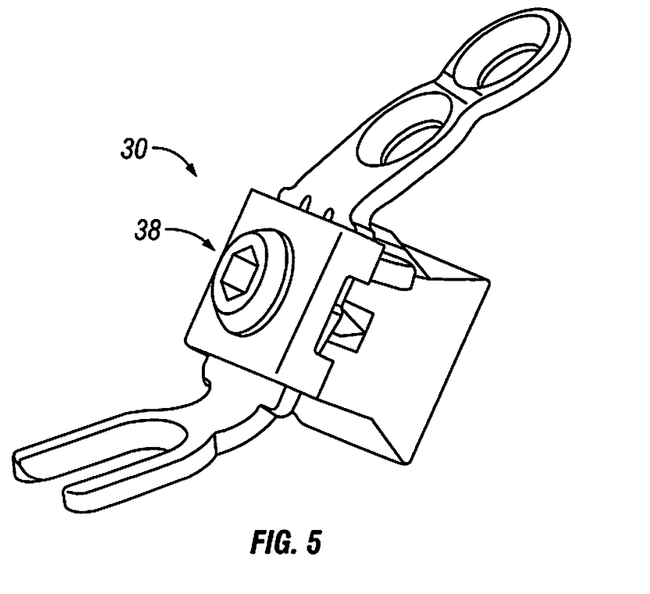
FIG. 5 depicts a perspective view of a laminoplasty plate assembled with a bone graft housing and having a washer and screw therein, attaching an allograft in accordance with non-limiting example embodiments of the invention.

According to the present invention, the present plates also have an option of attaching to an allograft (e.g., by a third party), for example by placing a washer and screw 38 through the opening/window 32 in the plate as depicted in FIG. 5.

Figure 6:
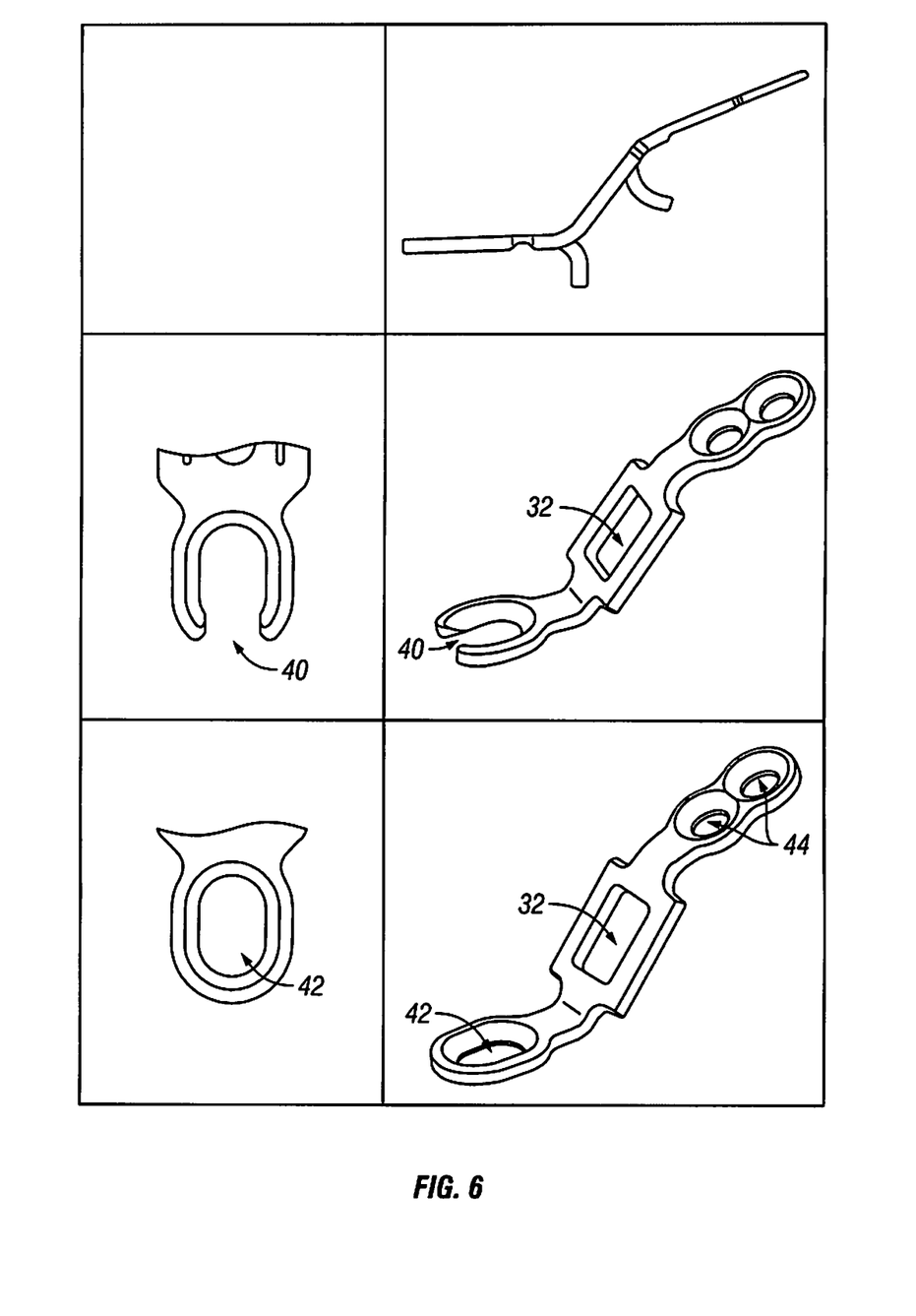
FIG. 6 depicts various non-limiting embodiments of laminoplasty plates according to non-limiting embodiments of the invention.

FIG. 6 depicts various non-limiting example embodiments of laminoplasty plates in accordance with the present invention. The top row depicts example plates from the side. The second and third rows depict plates from a perspective view having an open lateral mass screw hole 40 and an oblong lateral mass screw hole 42 respectively. Variations may be made or selected in the lateral mass screw hole, for example, according to surgeon preference. As with other embodiments provided herein, example laminoplasty plates may also include one or more holes 44 (or "screw holes"), which may be disposed for example for accessing and inserting fasteners from the outside of the bone to facilitate implantation. In embodiments in which more than one hole is provided on an end of the laminoplasty plate, the holes may be arranged in any suitable arrangement, including e.g., in a row as depicted in the embodiments of FIG. 6, or side by side, as depicted with respect to further embodiments herein, or in other arrangements.

According to example embodiments, laminoplasty plates may include one or more malleable laminoplasty plates that are made of Titanium. The bone graft housing may be made e.g., of Polyether ether ketone (PEEK).

Figure 7A:
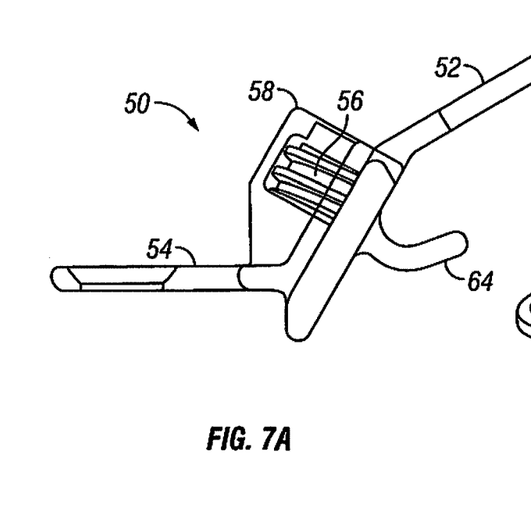
Figure 7B:
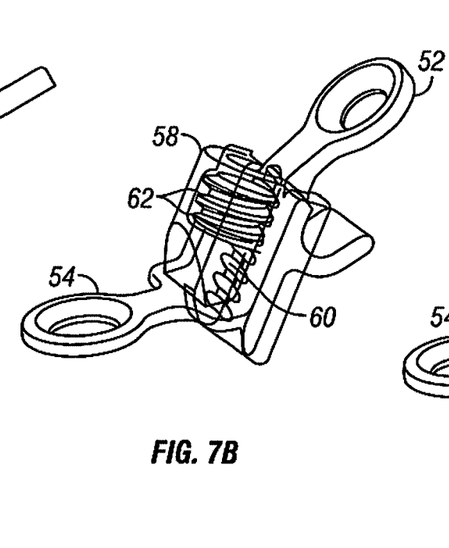
Figure 7C:
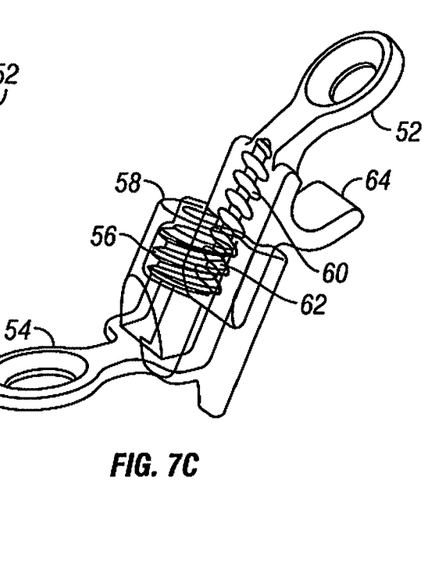

FIG. 7 depicts a side (7A) and perspective (7B and 7C) views of an expandable laminoplasty fixation system according to non-limiting embodiments of the invention. The expandable system 50 depicted in FIG. 7, includes at least three main components, a lateral mass plate 54, a lamina plate 52, and a set screw 56.

FIG. 7 depicts an example embodiment in which a set screw housing 58 is part of the lateral mass plate 54, but it is contemplated that the set screw housing may be a separate component e.g., attached to the lateral mass plate. The lamina plate 52 has angled grooves 60 that mate with the set screw thread 62, which forces the lamina plate 52 to expand or contract when set screw 56 is turned.

Thus, non-limiting example embodiments include an expandable laminoplasty fixation system that includes: a lateral mass plate having a set screw housing; a lamina plate having angled grooves; and a set screw positioned at least partially within said set screw housing, wherein said set screw has set screw thread, which set screw thread is mated with the angled grooves of the lamina plate such that when the set screw is screwed or unscrewed the lateral mass plate and lamina plate contract or expand with respect to one another.

According to non-limiting example embodiments, the lateral mass plate and/or the lamina plate may have a kick stand 64 that allows the plate assembly to self retain in the trough between lamina and lateral mass.

Advantages of these embodiments include that the device is adjustable and expandable by the turn of a screw. FIG. 7A depicts an example expandable laminoplasty fixation device from a side view with the lateral mass plate and lamina plate contracted. FIG. 7B depicts the same laminoplasty fixation device from a perspective view. In this view, the set screw 56 may be seen through the set screw housing 58. The set screw housing may or may not be at least partially transparent or translucent. As can be seen in this perspective view, the set screw thread 62 is mated with grooves 60 in the lamina plate 52. FIG. 7C depicts the same laminoplasty fixation device from a perspective view, but in FIG. 7C, the set screw 56 has been turned in a different position than in FIG. 7B such that the lateral mass plate 54 and the lamina plate 52 are expanded apart from one another.

Example methods herein may include positioning an expandable laminoplasty fixation device within a patient, adjusting the device to a desired position outside the patient and/or after placement in the patient, and fixing the expandable device to the patient using bone screws or other fixation devices placed through one or more openings/holes on either end of the device.

According to non-limiting example embodiments the plate may include a malleable material.

FIGS. 8-11 depict further non-limiting example embodiments of laminoplasty plates of the present invention. These example embodiments may also further include an attachable bone graft housing. Thus, encompassed herein are laminoplasty plates themselves, as well as devices, systems, kits and methods that include one or both of a laminoplasty plate and a bone graft housing either apart or attached to one another.

Figure 8A:
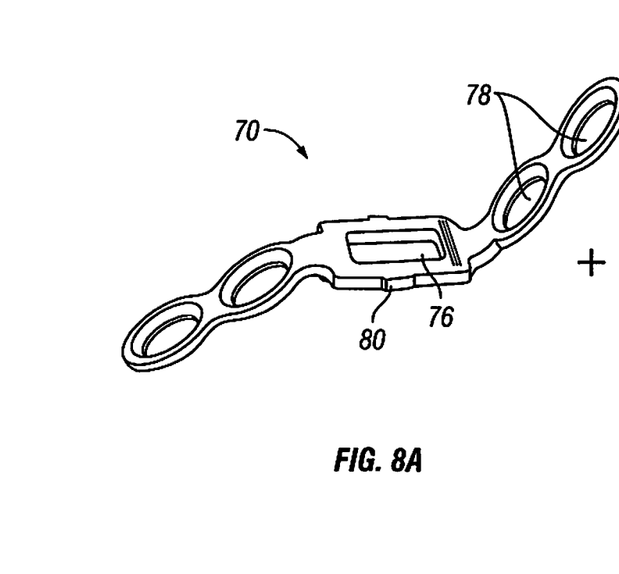
FIGS. 8A-8C depict a laminoplasty plate (8A) and a bone graft housing (8B) separately and assembled together (8C) according to non-limiting embodiments of the invention.
Figure 8B:
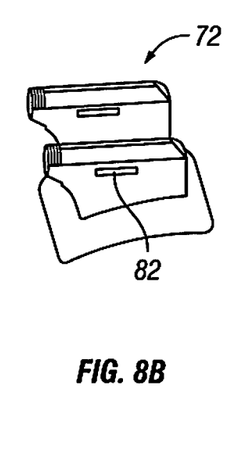
Figure 8C:
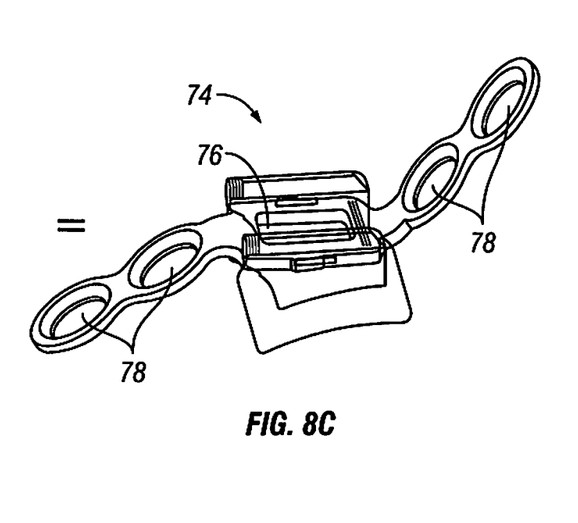

FIG. 8 depicts an example bone graft housing 72, which may be combined with a laminoplasty plate 70 in accordance with the present invention to form a plate and housing system or assembly 74. Laminoplasty plates in accordance with the present invention may include a least one opening 76 to facilitate packing of bone graft insertion into the housing 72.

Figures 9A, 9B:
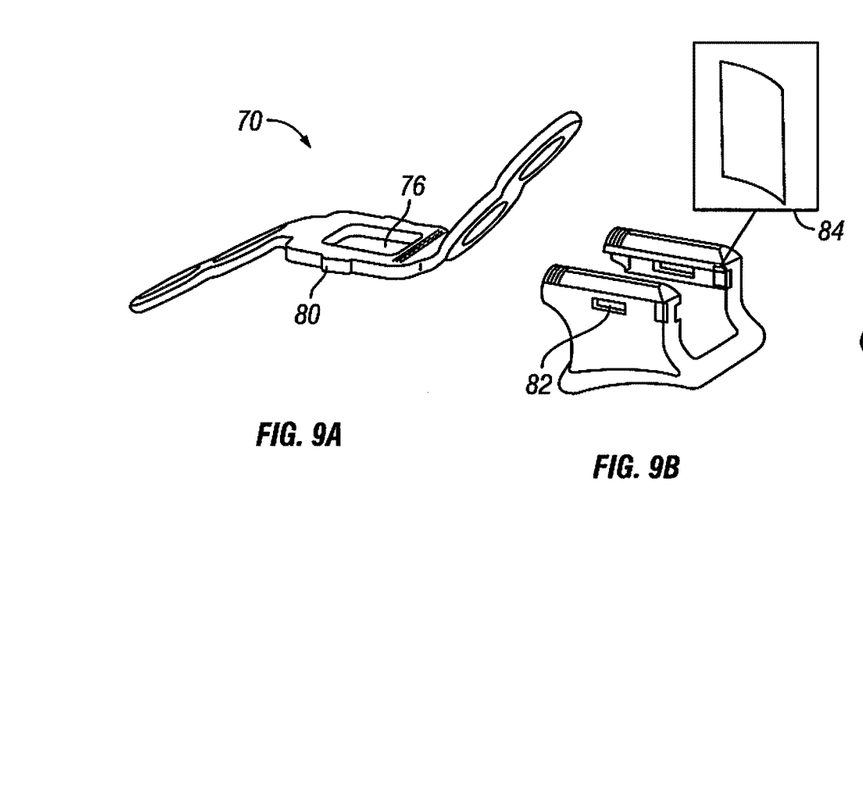
FIGS. 9A-9C depict a laminoplasty plate (9A) and a bone graft housing (9B) separately and assembled together (9C) according to non-limiting embodiments of the invention.
Figure 9C:
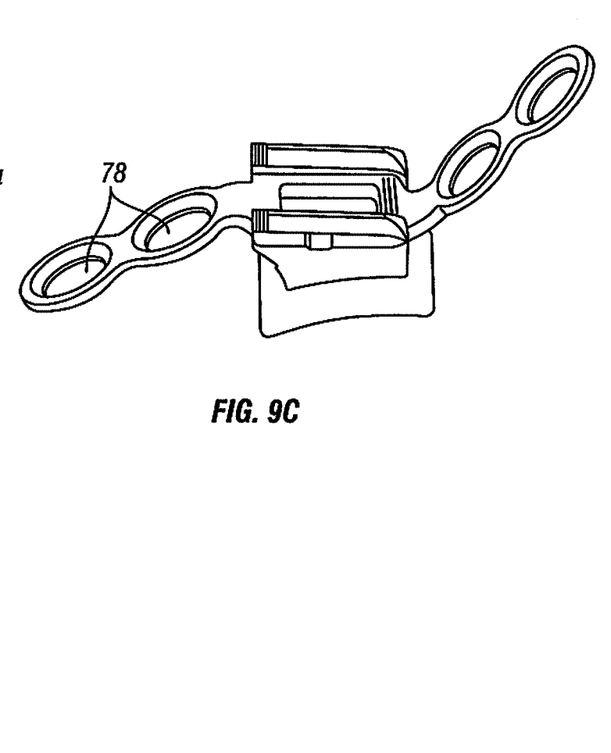

As depicted in FIGS. 8C and 9C, a laminoplasty plate 70 is slid into a bone graft housing 72.

FIG. 8 also shows an example laminoplasty plate having a lock 80, which may be configured to fit within e.g., holes or slits 82 of the bone graft housing to help lock the plate to the housing after they are slid together or otherwise attached to one another. FIG. 9 further depicts a stop 84 in the bone graft housing to assist with placing and/or maintaining the plate within the bone graft housing.

Also encompassed are methods that include inserting a laminoplasty plate/bone graft housing system into a patient and fixing the system to the patient's lamina in a desired position, e.g., using bone fasteners.

As with other embodiments of the present invention, the bone graft housing and laminoplasty plate may be configured so as to allow one to assemble the laminoplasty plate and bone graft housing in the operating room. By way of non-limiting example, the plate and housing may be assembled in an operating room by sliding a laminoplasty plate into a housing or alternatively, by snapping the plate on a housing, and locking the plate in place.

The plates in the present embodiments may have an option of having lateral mass side of holes lined up or perpendicular with respect to lamina alignment.

According to non-limiting example embodiments, the plate can be used in a laminoplasty procedure as a stand alone, i.e., without a bone graft housing. Further example embodiments include laminoplasty systems that include a laminoplasty plate and an attachable bone graft housing either attached to one another or not yet attached.

Figures 10A, 10B, 10C:
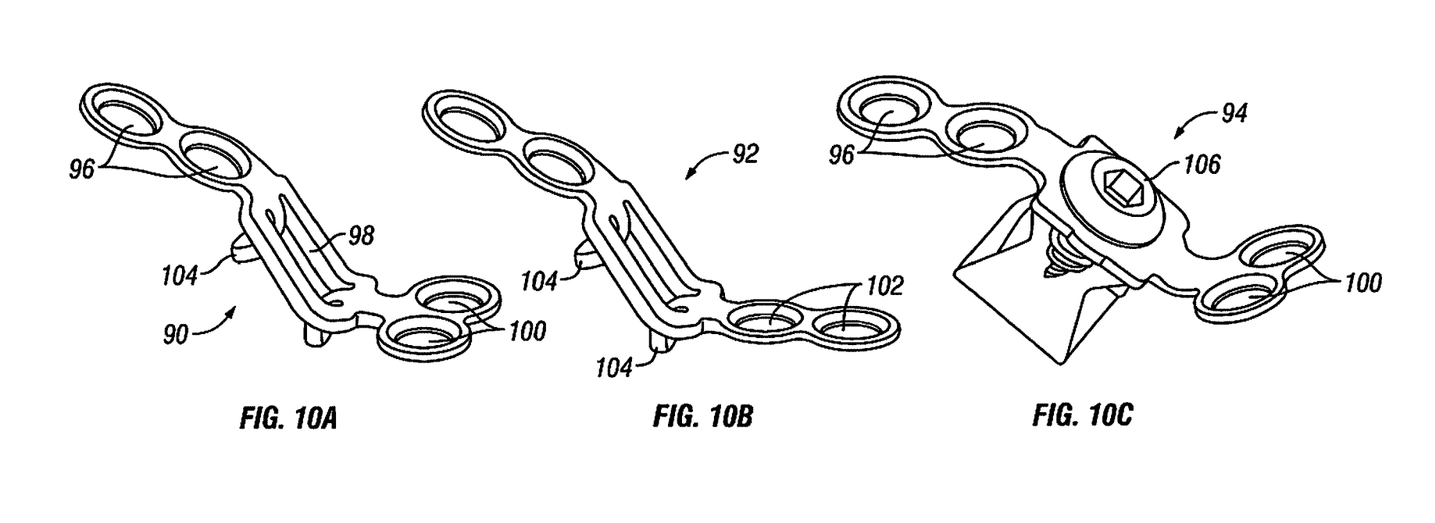
FIG. 10A-10C depict non-limiting embodiments of laminoplasty plates (10A and 10B) and a plate attached to an allograft by a bone screw (10C) according to non-limiting embodiments of the invention.

The plate may have for example an upper and/or lower kickstand 104 to sustain between lamina and lateral mass/ pedicle during the laminoplasty procedure. An optional kickstand on each side allows the plate design to be narrow and may simplify the manufacturability of the plate.

According to non-limiting example embodiments, such as depicted in FIG. 10, the present laminoplasty plates such as 90 or 92, may be attached to an allograft, for example by placing a graft screw 106 through an opening or window 98 to form the device or system 94 shown in FIG. 10C. Thus, these example laminoplasty plates may also include at least one opening 98 configured in size, position, and shape, to facilitate bone graft insertion into a bone graft housing when the laminoplasty plate is attached to the bone graft housing;

FIGS. 8 and 9 show one or more openings or holes 78 (or "screw holes") in example plates for receiving a bone fastener, such as a bone screw (e.g., polyaxial screw). The holes 78 may be disposed for example for accessing and inserting the fasteners from the outside of the bone to facilitate implantation. As depicted in FIGS. 8 and 9, the openings may be configured such that when there is more than one opening or hole 78, they may be in alignment with one another. FIG. 10 depicts another configuration of the holes 96 and 100, and in particular shows that according to non-limiting example embodiments, holes may be aligned with one another 96 and 102, or they may be side by side 100 as shown in FIGS. 10A and 10C. Other hole configurations are also contemplated however.

Figure 11:
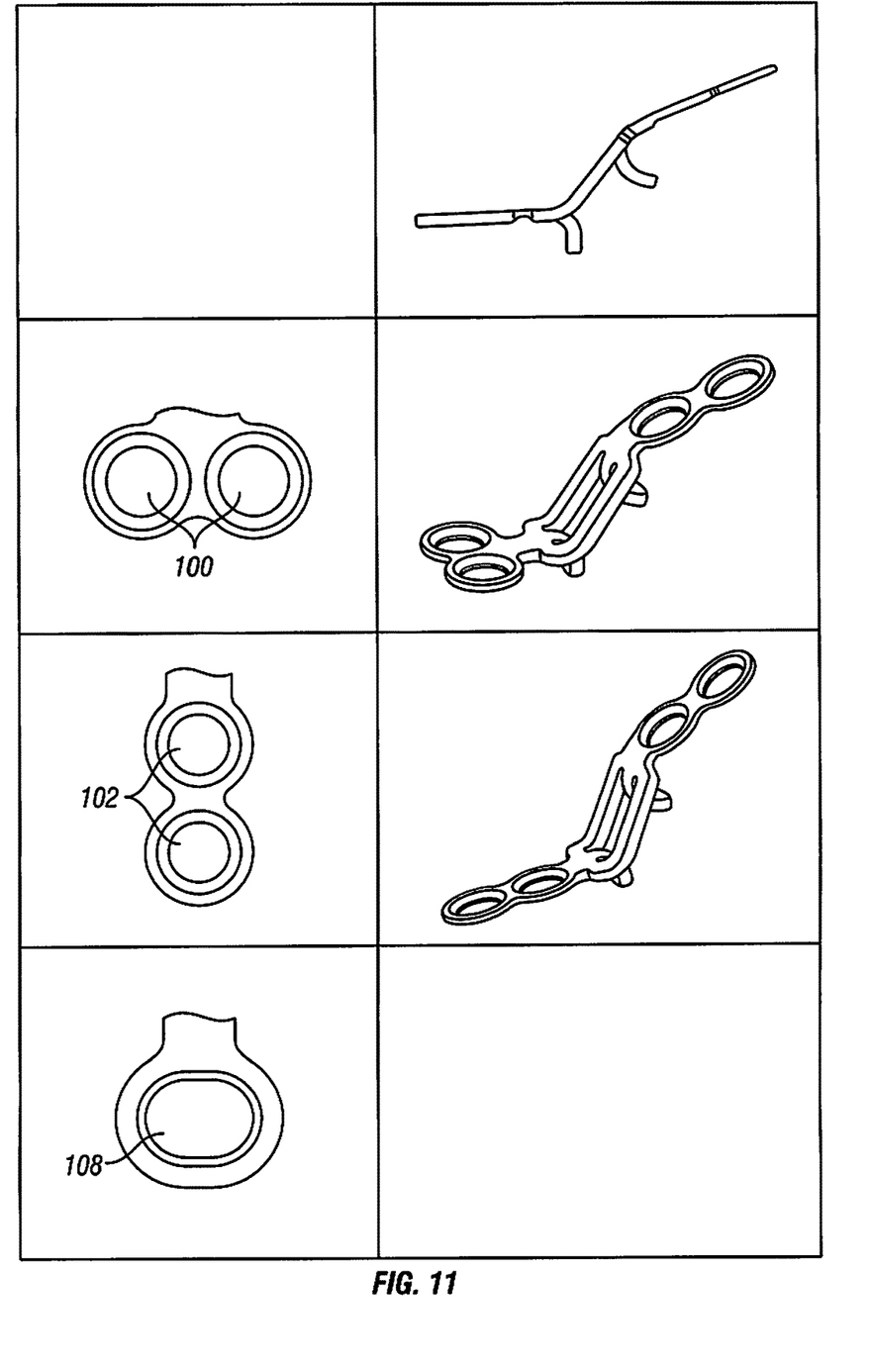
FIG. 11 depicts various non-limiting embodiments of laminoplasty plates according to non-limiting embodiments of the invention.

FIG. 11 depicts various non-limiting example embodiments of laminoplasty plates in accordance with the present invention. The top row depicts example plates from the side. The second, third and fourth rows depict plates from a perspective view having two side by side lateral mass screw holes 100, two aligned lateral mass screw holes 102, and an oblong lateral mass screw hole 108, respectively, for receiving one or more screws e.g., 110. Variations may be made or selected in the lateral mass screw hole, for example, according to surgeon preference.

As with other example embodiments, in these embodiments, laminoplasty plates may include one or more malleable laminoplasty plates that are made of Titanium. The bone graft housing may be made e.g., of Polyether ether ketone (PEEK).

According to non-limiting example embodiments, the present laminoplasty plates may be relatively simple to manufacture e.g., by stamping.

The present plates, devices and systems may be used in various laminoplasty procedures in accordance with the present invention. Thus, laminoplasty methods that use the present plates, devices and systems are encompassed hereby. By way of example, laminoplasty methods may be performed on a mammal. According to non-limiting example embodiments, the mammal may be for example, a human.

Also included herein are methods of assembling and/or adjusting laminoplasty devices and systems that may include e.g., more than one component or adjustable parts.

Further provided herein are kits for performing laminoplasty methods provided herein. Such kits may include for example, one or more laminoplasty elements, which may include for example one or more components or ingredients that may be used for in the methods and techniques herein.

By way of example, in embodiments having an articulating laminoplasty device described herein, example kits may include the articulating laminoplasty device itself, and at least one additional component such as instructions for using the device in a laminoplasty procedure, one or more bone fasteners or screws, and/or a screwdriver or other tool for fastening or screwing the device to a patient.

Other example kits may include a laminoplasty plate or device and at least one additional component such as a bone graft housing; instructions for assembling the laminoplasty plate and bone graft housing together; instructions for using the device or system in a laminoplasty procedure; a bone graft; one or more bone fasteners or screws; and/or a screwdriver or other tool for fastening or screwing the device to a patient. According to other example embodiments, kits may include a laminoplasty plate and bone graft housing already assembled or at least partially assembled together, but perhaps not locked into a position, thus allowing for one to adjust their relative positions during surgery.

Other example kits may include an expandable laminoplasty fixation system that includes a lateral mass plate, lamina plate and a set screw, and at least one additional component such as instructions for using the expandable laminoplasty fixation system in a laminoplasty procedure, one or more bone fasteners or screws, and/or a screwdriver or other tool for adjusting the screw in the laminoplasty fixation system and/or for fastening or screwing the device to a patient.

The kits may optionally include one or more devices or components for visualizing the devices or device placement or attachment during the laminoplasty procedure.

Although the invention has been described in example embodiments, those skilled in the art will appreciate that various modifications may be made without departing from the spirit and scope of the invention, and such modifications are therefore included herein. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A laminoplasty plate comprising:
at least one opening configured in size, position, and shape, to facilitate bone graft insertion into a separate bone graft housing when the laminoplasty plate is attached to the bone graft housing, wherein the laminoplasty plate is a single integral plate and further configured to slidably engage the bone graft housing; and
one or more screw holes disposed on each end of the laminoplasty plate, wherein the one or more screw holes are adapted for receiving a bone fastener or screw, wherein the one or more screw holes disposed on each end of the laminoplasty plate comprise at least two openings arranged linearly with respect to one another,
wherein the laminoplasty plate includes a central portion having an upper surface, a lower surface, a first sidewall, and a second sidewall,
wherein the laminoplasty plate comprises a lock in the form of a raised surface on one of the first or second sidewalls that is configured to fit within a slot in the bone graft housing in order to secure the laminoplasty plate to the bone graft housing, wherein the lock extends from the upper surface to the lower surface of the central portion of the laminoplasty plate,
wherein the one or more screws holes disposed on each end of the laminoplasty plate are positioned on different planes,
wherein the laminoplasty plate is configured to be positioned on a lamina of a vertebra,
wherein the first and second sidewalls of the laminoplasty plate are configured to slide along one or more tracks formed along an inner wall of the bone graft housing and a portion of the upper and lower surfaces are received in the one or more tracks such that the lock is received within the slot,
wherein a stop is disposed within one or more of the tracks, the stop configured to assist in at least one of placing and maintaining the plate within the bone graft housing, and
wherein the stop is disposed outside of the slot.

2. The laminoplasty plate of claim 1, wherein the laminoplasty plate includes a kickstand, and the kickstand is positioned and configured on the laminoplasty plate to sustain the plate between a patient's lamina and lateral mass/pedicle during a laminoplasty procedure.

3. The laminoplasty plate of claim 1, wherein the one or more screw holes comprise at least one open lateral mass screw hole.

4. The laminoplasty plate of claim 1, wherein the one or more screw holes comprise an oblong lateral mass screw hole.

5. A kit comprising the laminoplasty plate of claim 1, and at least one additional component selected from the group consisting of: a bone graft housing; instructions for assembling the laminoplasty plate and bone graft housing together; instructions for using the plate or system in a laminoplasty procedure; a bone graft; one or more bone fasteners or screws: and a screwdriver.

6. The laminoplasty plate of claim 1, wherein the laminoplasty plate includes a kickstand, and a portion of the kickstand is defined by two slots extending from the at least one opening.

7. The laminoplasty plate of claim 6, wherein a second kickstand extends from a second end of the at least one opening in the laminoplasty plate.

8. The laminoplasty plate of claim 1, wherein the at least one opening is an elongated opening that extends along a longitudinal axis of the central portion.

9. The laminoplasty plate of claim 1, wherein the central portion extends from a first end to a second end, and the lock includes a single central lock on the first sidewall between the first and second ends and a single central lock on the second sidewall between the first and second ends.

10. A laminoplasty system comprising
a laminoplasty plate and a separate, attachable bone graft housing, wherein the laminoplasty plate is a single integral plate and further configured to slidably engage the bone graft housing,
wherein the laminoplasty plate includes a central portion having an upper surface, a lower surface, a first sidewall, and a second sidewall, wherein the laminoplasty plate comprises a lock in the form of a raised surface on one of the first or second sidewalls that is configured to fit within a slot in the bone graft housing in order to secure the laminoplasty plate to the bone graft housing, wherein the lock extends from the upper surface to the lower surface of the central portion of the laminoplasty plate, wherein the slot has a completely enclosed perimeter within the bone graft housing, wherein one or more screws holes disposed on each end of the laminoplasty plate are positioned on different planes, wherein the laminoplasty plate is configured to be positioned on a lamina of a vertebra, wherein the first and second sidewalls of the laminoplasty plate are configured to slide along one or more tracks formed along an inner wall of the bone graft housing and a portion of the upper and lower surfaces are received in the one or more tracks such that the lock is received within the slot, wherein a stop is disposed within one or more of the tracks, the stop configured to assist in at least one of placing and maintaining the plate within the bone graft housing, and wherein the stop is disposed outside of the slot.

11. The laminoplasty system of claim 10, wherein the plate and housing are configured such that they may be assembled together by sliding the laminoplasty plate into the housing.

12. A laminoplasty plate comprising
at least one opening configured in size, position, and shape, to facilitate bone graft insertion into a separate bone graft housing when the laminoplasty plate is attached to the bone graft housing, wherein the laminoplasty plate is a single integral plate and further configured to slidably engage the bone graft housing; and
at least two screw holes disposed on each end of the laminoplasty plate, wherein the one or more screw holes are adapted for receiving a bone fastener or screw,
wherein the laminoplasty plate includes a central portion having an upper surface, a lower surface, a first sidewall, and a second sidewall, wherein the laminoplasty plate comprises a lock that is configured to fit within a slot in the bone graft housing to secure the laminoplasty plate to the bone graft housing, wherein the lock extends from the upper surface to the lower surface of the central portion of the laminoplasty plate, wherein the first and second sidewalls of the laminoplasty plate are configured to slide along one or more tracks formed along an inner wall of the bone graft housing and a portion of the upper and lower surfaces are received in the one or more tracks such that the lock is received within the slot, wherein a stop is disposed within one or more of the tracks, the stop configured to assist in at least one of placing and maintaining the plate within the bone graft housing, wherein the stop is disposed outside of the slot, wherein the one or more screws holes disposed on each end of the laminoplasty plate are positioned on different planes, and wherein the laminoplasty plate is configured to be positioned on a lamina of a vertebra.

13. The laminoplasty plate of claim 12, wherein the lock comprises a raised surface on a sidewall that is configured to fit within a slot in the bone graft housing.

14. The laminoplasty plate of claim 13, wherein the slot has a completely enclosed perimeter within the bone graft housing.

15. The laminoplasty plate of claim 13, wherein the slot comprises four sides.

16. The laminoplasty plate of claim 12, wherein exactly two screw holes are disposed on each end.

17. The laminoplasty plate of claim 12, further comprising an opening positioned between a first set of at least two screw holes disposed on a first end of the laminoplasty plate and a second set of at least two screw holes disposed on a second end of the laminoplasty plate.

18. The laminoplasty plate of claim 17, wherein the opening is aligned with a channel formed along a longitudinal length of the bone graft housing.

* * * * *